United States Patent
Izmirli et al.

(10) Patent No.: US 11,771,338 B2
(45) Date of Patent: *Oct. 3, 2023

(54) LOCALIZED MAGNETIC FIELD GENERATOR

(71) Applicant: St. Jude Medical International Holding S.à r.l., Luxembourg (LU)

(72) Inventors: Alon Izmirli, Ganot Hadar (IL); Uzi Eichler, Haifa (IL); Michael Korol, Haifa (IL); Kobi Kor, Ramat Hsharon (IL); Yuval Vaknin, Hanaton (IL)

(73) Assignee: ST JUDE MEDICAL INTERNATIONAL HOLDING S.À R.L., Luxembourg (LU)

( * ) Notice: Subject to any disclaimer, the term of this patent is extended or adjusted under 35 U.S.C. 154(b) by 520 days.

This patent is subject to a terminal disclaimer.

(21) Appl. No.: 16/905,521

(22) Filed: Jun. 18, 2020

(65) Prior Publication Data

US 2020/0383603 A1    Dec. 10, 2020

Related U.S. Application Data

(62) Division of application No. 15/323,178, filed as application No. PCT/IB2015/001675 on Jul. 1, 2015, now Pat. No. 10,722,140.

(Continued)

(51) Int. Cl.
*A61B 5/00*    (2006.01)
*A61B 5/06*    (2006.01)
(Continued)

(52) U.S. Cl.
CPC .............. *A61B 5/062* (2013.01); *A61B 5/063* (2013.01); *A61B 5/6852* (2013.01); *A61B 6/4441* (2013.01); *A61B 34/20* (2016.02); *A61B 5/283* (2021.01); *A61B 2034/2051* (2016.02); *A61B 2034/2072* (2016.02);
(Continued)

(58) Field of Classification Search
CPC ....... A61B 5/062; A61B 5/063; A61B 5/6852; A61B 6/4441; A61B 34/20; A61B 5/283; A61B 2034/2051; A61B 2034/2072; A61B 2090/0436; A61B 2090/0481; A61B 2090/397
See application file for complete search history.

(56) References Cited

U.S. PATENT DOCUMENTS 5,760,335 A    6/1998    Gilboa
6,147,480 A    11/2000   Osadchy et al.
(Continued)

FOREIGN PATENT DOCUMENTS

CN    1878458 A    12/2006
CN    102892453 A   1/2013
(Continued)

*Primary Examiner* — Joel Lamprecht
(74) *Attorney, Agent, or Firm* — Billion & Armitage

(57) ABSTRACT

An apparatus for generating a magnetic field for tracking of an object can include a localized magnetic field generator that is configured to generate a magnetic field and to control the magnetic field in an area of interest and configured to control the magnetic field in a separate area. The separate area can be displaced from the area of interest and can include a magnetic field-disrupting component. The object can be located in the area of interest.

13 Claims, 11 Drawing Sheets

Related U.S. Application Data

(60) Provisional application No. 62/098,813, filed on Dec. 31, 2014, provisional application No. 62/020,881, filed on Jul. 3, 2014.

(51) Int. Cl.
  *A61B 34/20* (2016.01)
  *A61B 6/00* (2006.01)
  *A61B 90/00* (2016.01)
  *A61B 5/283* (2021.01)

(52) U.S. Cl.
  CPC ............ *A61B 2090/0436* (2016.02); *A61B 2090/0481* (2016.02); *A61B 2090/397* (2016.02)

(56) References Cited

U.S. PATENT DOCUMENTS

| | | |
|---|---|---|
| 6,177,792 B1 | 1/2001 | Govari et al. |
| 6,201,987 B1 | 3/2001 | Dumoulin |
| 6,233,476 B1 | 5/2001 | Strommer et al. |
| 6,288,785 B1 | 9/2001 | Frantz et al. |
| 6,340,888 B1 | 1/2002 | Aoki et al. |
| 6,373,240 B1 | 4/2002 | Govari |
| 6,498,477 B1 | 12/2002 | Govari et al. |
| 6,553,326 B1 | 4/2003 | Kirsch et al. |
| 6,636,757 B1* | 10/2003 | Jascob ............... A61B 34/20 324/207.13 |
| 7,197,354 B2 | 3/2007 | Sobe |
| 7,386,339 B2 | 6/2008 | Strommer et al. |
| 7,976,518 B2 | 7/2011 | Shaughnessy et al. |
| 8,543,188 B2 | 9/2013 | von Jako et al. |
| 10,722,140 B2* | 7/2020 | Izmirli ............... A61B 5/063 |
| 2003/0120150 A1 | 6/2003 | Govari |
| 2003/0173953 A1 | 9/2003 | Ashe |
| 2003/0200052 A1 | 10/2003 | Seiler et al. |
| 2004/0068178 A1 | 4/2004 | Govari |
| 2004/0102696 A1 | 5/2004 | Govari |
| 2004/0207389 A1 | 10/2004 | Nieminen et al. |
| 2004/0239314 A1 | 12/2004 | Govari |
| 2004/0254453 A1 | 12/2004 | Govari |
| 2005/0003757 A1 | 1/2005 | Anderson |
| 2005/0024043 A1 | 2/2005 | Govari |
| 2006/0116832 A1 | 6/2006 | Nieminen et al. |
| 2006/0116833 A1 | 6/2006 | Nieminen et al. |
| 2006/0293593 A1 | 12/2006 | Govari et al. |
| 2007/0078334 A1* | 4/2007 | Scully ............... A61B 5/06 600/424 |
| 2007/0085528 A1 | 4/2007 | Govari et al. |
| 2007/0238922 A1 | 10/2007 | Oda et al. |
| 2007/0244385 A1 | 10/2007 | Satragno et al. |
| 2007/0244388 A1 | 10/2007 | Sato et al. |
| 2007/0255132 A1 | 11/2007 | Shalgi et al. |
| 2008/0103388 A1 | 5/2008 | Maschke et al. |
| 2008/0125646 A1 | 5/2008 | Govari et al. |
| 2008/0144769 A1 | 6/2008 | Schmidt |
| 2008/0287771 A1* | 11/2008 | Anderson ............. A61B 5/055 600/410 |
| 2008/0300477 A1 | 12/2008 | Lloyd et al. |
| 2008/0306380 A1 | 12/2008 | Parchak et al. |
| 2009/0306494 A1 | 12/2009 | Scarth et al. |
| 2010/0008475 A1 | 1/2010 | Maschke |
| 2010/0204566 A1 | 8/2010 | Uchiyama et al. |
| 2011/0004430 A1 | 1/2011 | Nieminen et al. |
| 2012/0201432 A1 | 8/2012 | Neidert |
| 2013/0272592 A1 | 10/2013 | Eichler et al. |
| 2016/0287133 A1 | 10/2016 | Eichler et al. |
| 2017/0108356 A1 | 4/2017 | Iida et al. |
| 2019/0069877 A1 | 3/2019 | Burnside et al. |

FOREIGN PATENT DOCUMENTS

| | | |
|---|---|---|
| EP | 1382308 A2 | 1/2004 |
| EP | 2749240 A2 | 7/2014 |
| JP | H09238919 A | 9/1997 |
| JP | 2002-257914 A | 9/2002 |
| WO | 1997036143 A1 | 10/1997 |
| WO | 2001077701 A | 10/2001 |
| WO | 2002008793 A1 | 1/2002 |
| WO | 2004091391 A1 | 10/2004 |
| WO | 2011112814 A1 | 9/2011 |
| WO | 2012175846 A1 | 12/2012 |
| WO | 2013013718 A1 | 1/2013 |

* cited by examiner

LOCALIZED MAGNETIC FIELD GENERATOR

CROSS-REFERENCE TO RELATED APPLICATIONS

This application is a United States divisional patent application of U.S. application Ser. No. 15/323,178, filed 30 Dec. 2016 (the '178 application), now issued as U.S. Pat. No. 10,722,140 on 28 Jul. 2020; the '178 application is a United States national stage patent application based on International application no. PCT/IB2015/001675, filed 1 Jul. 2015 (the '675 application), and published under International publication no. WO 2016/001759 A1 on 7 Jan. 2016. This application claims priority to U.S. provisional patent application no. 62/020,881, filed 3 Jul. 2014, entitled "LOCALIZED MAGNETIC FIELD GENERATOR" and to U.S. provisional patent application no. 62/098,813, filed 31 Dec. 2014, entitled "LOCALIZED MAGNETIC FIELD GENERATOR." The '178 application; the '675 application; the '615application; and the '650 application are incorporated by reference as though fully set forth herein.

BACKGROUND a. Field

The instant disclosure relates to a localized magnetic field generator and related components.

b. Background Art

Medical devices, catheters, and/or cardiovascular catheters, such as electrophysiology catheters can be used in a variety of diagnostic, therapeutic, mapping and/or ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart, which can lead to a variety of symptomatic and asymptomatic ailments and even death.

A medical device can be threaded through a vasculature of a patient to a site where the diagnostic, therapeutic, mapping, and/or ablative procedure to diagnose and/or correct the condition is performed. To aid in the delivery of the medical device to the site, sensors (e.g., electrodes) can be placed on the medical device, which can receive signals that are generated proximate to the patient from a device (e.g., electromagnetic field generator). Based on the received signals, an orientation and/or position of the medical device can be computed.

DETAILED DESCRIPTION

Figure 1:
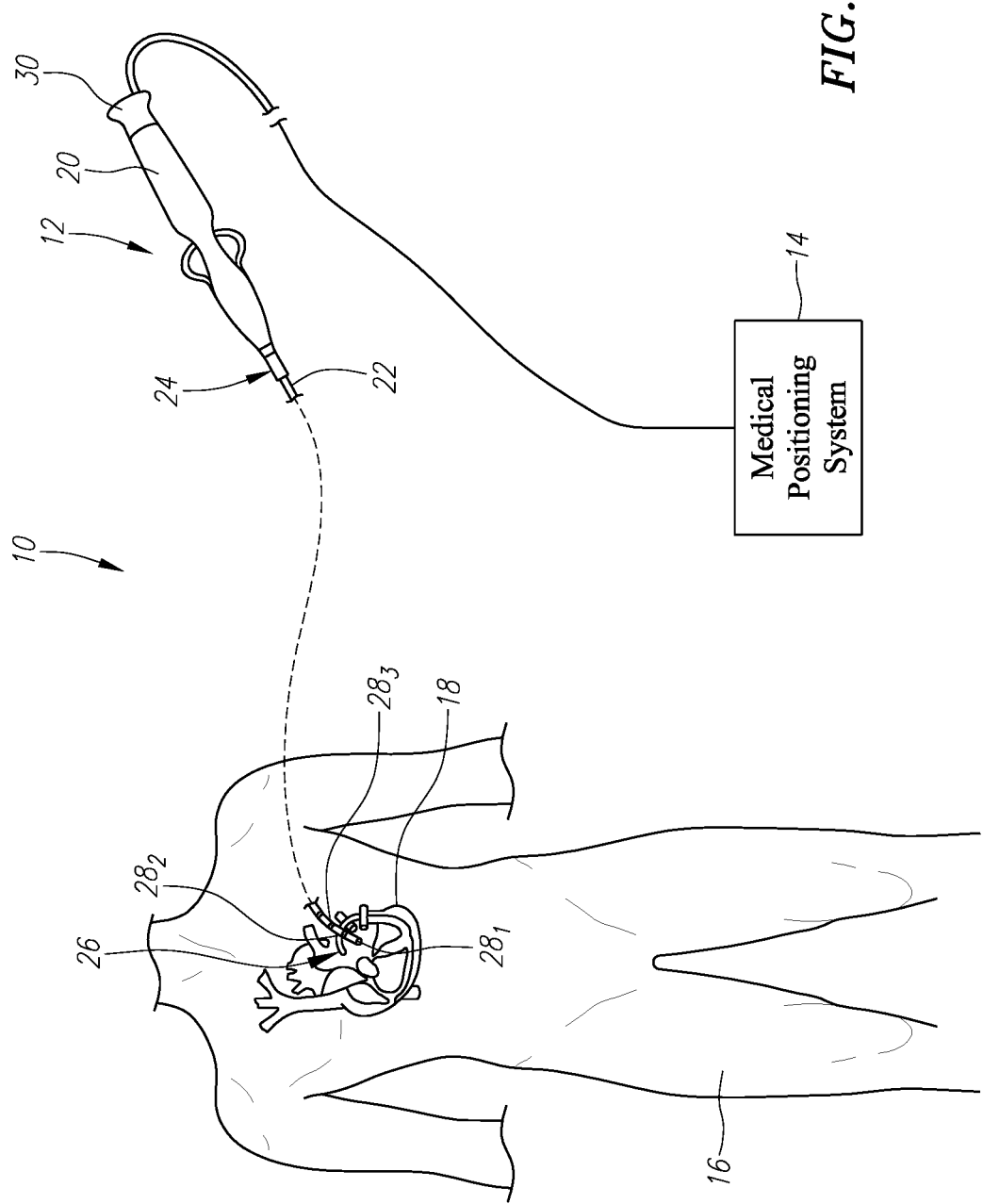
FIG. 1 depicts a diagrammatic view of an exemplary system for performing one or more diagnostic or therapeutic procedures, wherein the system comprises a magnetic field-based medical positioning system, in accordance with embodiments of the present disclosure.

In some embodiments, and with reference to FIG. 1, the system 10 can include a medical device 12 and a medical positioning system 14. The medical device 12 can include an elongate medical device such as, for example, a catheter or a sheath. For purposes of illustration and clarity, the description below will be limited to an embodiment wherein the medical device 12 comprises a catheter (e.g., catheter 12). It will be appreciated, however, that the present disclosure is not meant to be limited to such an embodiment, but rather in other exemplary embodiments, the medical device may comprise other elongate medical devices, such as, for example and without limitation, sheaths, introducers and the like.

With continued reference to FIG. 1, the catheter 12 can be configured to be inserted into a patient's body 16, and more particularly, into the patient's heart 18. The catheter 12 may include a handle 20, a shaft 22 having a proximal end portion 24 and a distal end portion 26, and one or more sensors 28 mounted in and/or on the shaft 22 of the catheter 12. As used herein, "sensor 28" or "sensors 28" may refer to one or more sensors $28_1, 28_2, \ldots 28_N$, as appropriate and as generally depicted. In an exemplary embodiment, the sensors 28 are disposed at the distal end portion 26 of the shaft 22. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

The shaft 22 can be an elongate, tubular, flexible member configured for movement within the body 16. The shaft 22 supports, for example and without limitation, sensors and/or electrodes mounted thereon, such as, for example, the sensors 28, associated conductors, and possibly additional electronics used for signal processing and conditioning. The shaft 22 may also permit transport, delivery, and/or removal of fluids (including irrigation fluids, cryogenic ablation fluids, and bodily fluids), medicines, and/or surgical tools or instruments. The shaft 22 may be made from conventional materials such as polyurethane, and define one or more lumens configured to house and/or transport electrical conductors, fluids, or surgical tools. The shaft 22 may be introduced into a blood vessel or other structure within the body 16 through a conventional introducer. The shaft 22 may then be steered or guided through the body 16 to a desired location, such as the heart 18, using means well known in the art.

The sensors 28 mounted in or on the shaft 22 of the catheter 12 may be provided for a variety of diagnostic and therapeutic purposes including, for example and without limitation, electrophysiological studies, pacing, cardiac mapping, and ablation. In an exemplary embodiment, one or more of the sensors 28 are provided to perform a location or position sensing function. More particularly, and as will be described in greater detail below, one or more of the sensors 28 are configured to be a positioning sensor that provides information relating to the location (e.g., position and orientation) of the catheter 12, and the distal end portion 26 of the shaft 22 thereof, in particular, at certain points in time. Accordingly, in such an embodiment, as the catheter 12 is moved along a surface of a structure of interest of the heart 18 and/or about the interior of the structure, the sensor(s) 28 can be used to collect location data points that correspond to the surface of, and/or other locations within, the structure of interest. These location data points can then be used for a number of purposes such as, for example and without limitation, the construction of surface models of the structure of interest. For purposes of clarity and illustration, the description below will be with respect to an embodiment wherein a single sensor 28 of the catheter 12 comprises a positioning sensor. It will be appreciated, however, that in other exemplary embodiments, which remain within the spirit and scope of the present disclosure, the catheter 12 may comprise more than one positioning sensor as well as other sensors or electrodes configured to perform other diagnostic and/or therapeutic functions. As will be described in greater detail below, the sensor 28 can include a pair of leads extending from a sensing element thereof (e.g., a coil) that are configured to electrically couple the sensor 28 to other components of the system 10, such as, for example, the medical positioning system 14.

Figure 2:
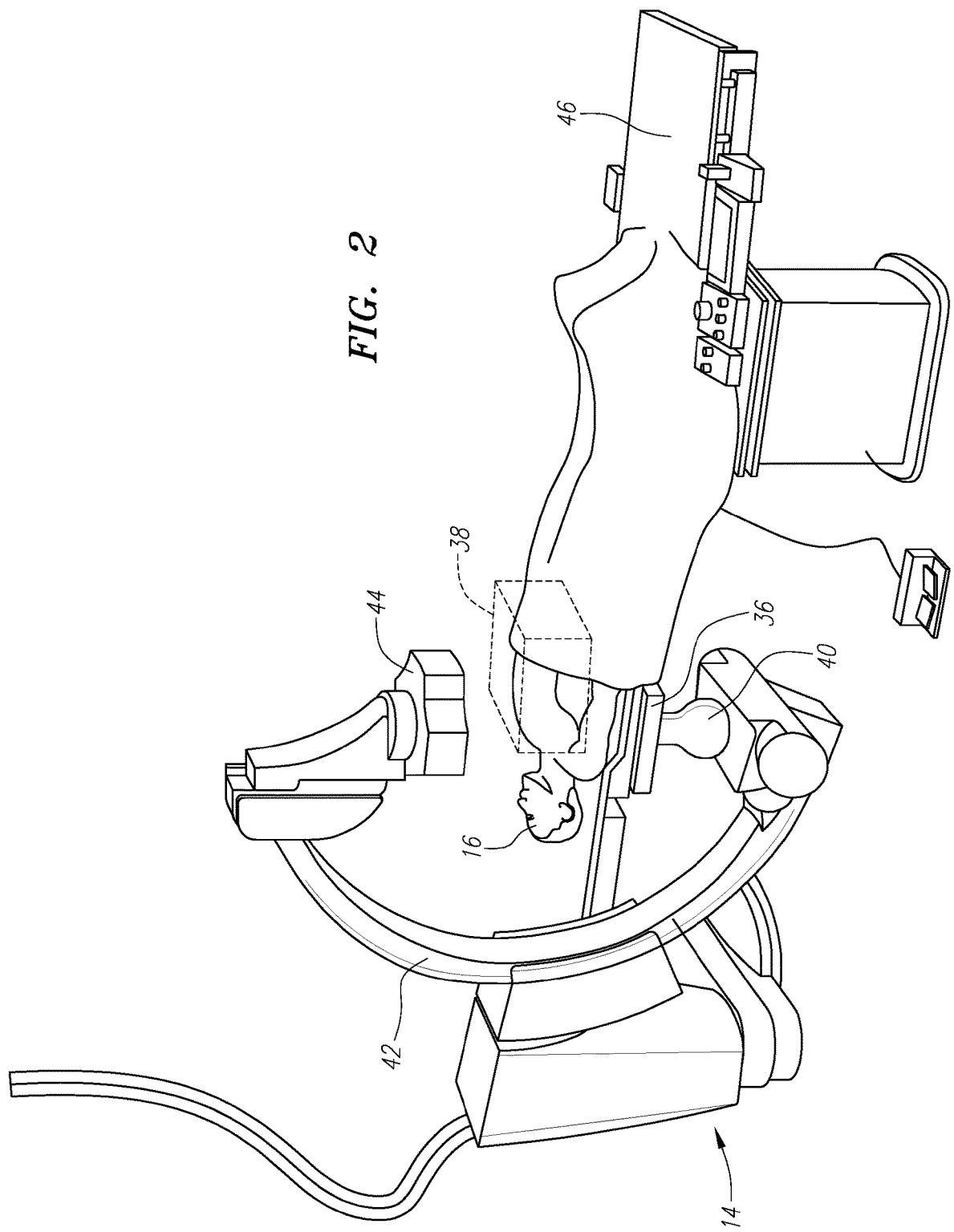
FIG. 2 depicts a medical positioning system, in accordance with embodiments of the present disclosure.

With reference to FIGS. 1 and 2, the medical positioning system 14 will now be described. The medical positioning system 14 can be provided for determining a position and/or orientation of the sensor 28 of the catheter 12, and thus, the position and/or orientation of the catheter 12. In some embodiments, the medical positioning system 14 may comprise a magnetic field-based system such as, for example, the MediGuide™ system from MediGuide Ltd. (now owned by St. Jude Medical, Inc.), and as generally shown with reference to one or more of U.S. Pat. Nos. 6,233,476; 7,197,354; and 7,386,339, the entire disclosures of which are incorporated herein by reference.

In some embodiments, and in general terms, the medical positioning system 14 comprises, at least in part, an apparatus 36 for generating a magnetic field for tracking of an object (e.g., catheter 12). The apparatus 36 can be configured to generate low-strength magnetic field(s) in and around the patient's chest cavity in an area of interest, which can be defined as a three-dimensional space designated as area of interest 38 in FIG. 2. In such an embodiment, and as briefly described above, the catheter 12 includes a positioning sensor 28 comprising a magnetic sensor configured to detect one or more characteristics of the low-strength magnetic field(s) applied by the apparatus 36 when the sensor 28 is disposed within the area of interest 38. The sensor 28, which in an exemplary embodiment comprises a magnetic coil, can be electrically connected with a processing core and configured to generate a signal corresponding to the sensed characteristics of the magnetic field(s) to which the magnetic processing core is exposed. The processing core can be responsive to the detected signal and can be configured to calculate a three-dimensional position and/or orientation reading for the sensor 28. Thus, the medical positioning system 14 enables real-time tracking of each magnetic sensor 28 of the catheter 12 in three-dimensional space, and therefore, real-time tracking of the catheter 12.

In some embodiments, the apparatus 36 can be located underneath a patient examination table 46, between an x-ray source 40 and the patient examination table 46. For example, the apparatus 36 can be connected with the patient examination table 46. In some embodiments, as discussed herein, the apparatus 36 can be a mobile device, which can be placed on a chest of the patient and used to generate the magnetic field for tracking of the object.

In an example, challenges can be associated with generating a magnetic field for tracking an object, because the magnetic field can be disrupted as a result of objects that are located proximate to the magnetic field and/or a generator that produces the magnetic field. For example, magnetic field-disrupting components can be located proximately to a magnetic field generator (e.g., apparatus 36) and can include the x-ray source 40, portions of the patient examination table 46, a c-arm 42, and/or an x-ray image intensifier 44 associated with the medical positioning system 14. As such, the magnetic field-disrupting components can have an effect on the magnetic field and cause disruptions in the magnetic field. In some cases, even objects that are located far away from the magnetic field generator and/or the magnetic field produced by the magnetic field generator can cause disruptions to the magnetic field. Part of the disruption can be to the magnetic field located within the area of interest 38. This can be problematic, because each magnetic sensor 28 of the catheter 12 is reliant on a consistent (e.g., undisrupted) magnetic field to determine a position and/or orientation of the sensor 28 and/or catheter 12.

In an example, a source of the disturbance to the magnetic field can be an eddy current effect and/or a change in a magnetic permeability caused by magnetic field-disrupting components. In an example, the magnetic field disrupting components can include conductive and/or magnetically permeable objects located within a proximity to the apparatus 36 and/or a magnetic field produced by the apparatus 36. As used herein, magnetically permeable can be defined as an inclination that a material has to support a formation of a magnetic field within itself. As used herein, conductive can be defined as a disinclination that a material has to support a formation of a magnetic field within itself. For example, a magnetically permeable material can bend magnetic field lines toward the material, while a conductive material can bend magnetic field lines away from the material.

In some examples, where the magnetic field-disrupting component is stationary, an eddy current caused by the magnetic field-disrupting component can be factored out when determining a location of the catheter 12, in an example. However, in a medical positioning system 14, such as that depicted in FIG. 2, the x-ray source 40, the c-arm 42, the x-ray image intensifier 44, as well as the patient examination table 46 can all move with respect to the apparatus 36 and can cause varying disturbances to the magnetic field produced by the apparatus 36, which can be unpredictable. As such, eddy currents produced by the magnetic field-disrupting components can constantly vary and can be difficult to factor out.

In some examples, the medical positioning system 14 can include an impedance-based system for determination of a position and/or orientation of the catheter 12. However, in some previous approaches, eddy currents generated from a magnetic field-based system used in conjunction with the impedance-based system can cause a shift and/or drift associated with coordinates determined through the impedance-based system. In addition, a distorted representation of a geometry of the heart can be generated when using an impedance based system. For instance, electrical currents used in an impedance based system can travel three-dimensionally along a path of least resistivity. As such, part of the electrical currents can leave a transverse plane with blood flow, for example, through an impedance transfer. Factoring in impedance transfer can involve a non-linear solution, which can result in the distorted representation of the geometry of the heart.

Accordingly, embodiments of the present disclosure can reduce and/or eliminate eddy currents in the magnetic field produced by the apparatus 36 by reducing a strength of the magnetic field produced by the apparatus 36 in a vicinity of the magnetic field-disrupting components. Some embodiments of the present disclosure can result in a reduction in the shift and/or drift associated with coordinates determined through the impedance-based system, as a result of the reduction and/or elimination of eddy currents. Further, some embodiments of the present disclosure can include a magnetic field-based system that is linear. In an example, this can be accomplished by reducing a strength of a magnetic field produced by the apparatus 36 and/or shielding the magnetic field produced by the apparatus 36 from the magnetic field-disrupting components. As such, some embodiments of the present disclosure can be configured to increase a ratio of a strength of a magnetic field located in an area of interest that includes an object being tracked with the magnetic field versus a strength of a magnetic field located in a separate area that includes a magnetic field-disrupting component. Embodiments of the present disclosure can accomplish this through asymmetric electromagnetic shielding. In some embodiments of the present disclosure, this can be accomplished by using a magnetic field generator that produces a magnetic field of a lesser magnitude and placing the magnetic field generator proximate to the area of interest 38, such that a size of a magnetic field produced outside the area of interest 38 by the apparatus 36 is reduced, thus reducing chances for disturbance of the magnetic field by the magnetic field-disrupting components.

Figure 5:
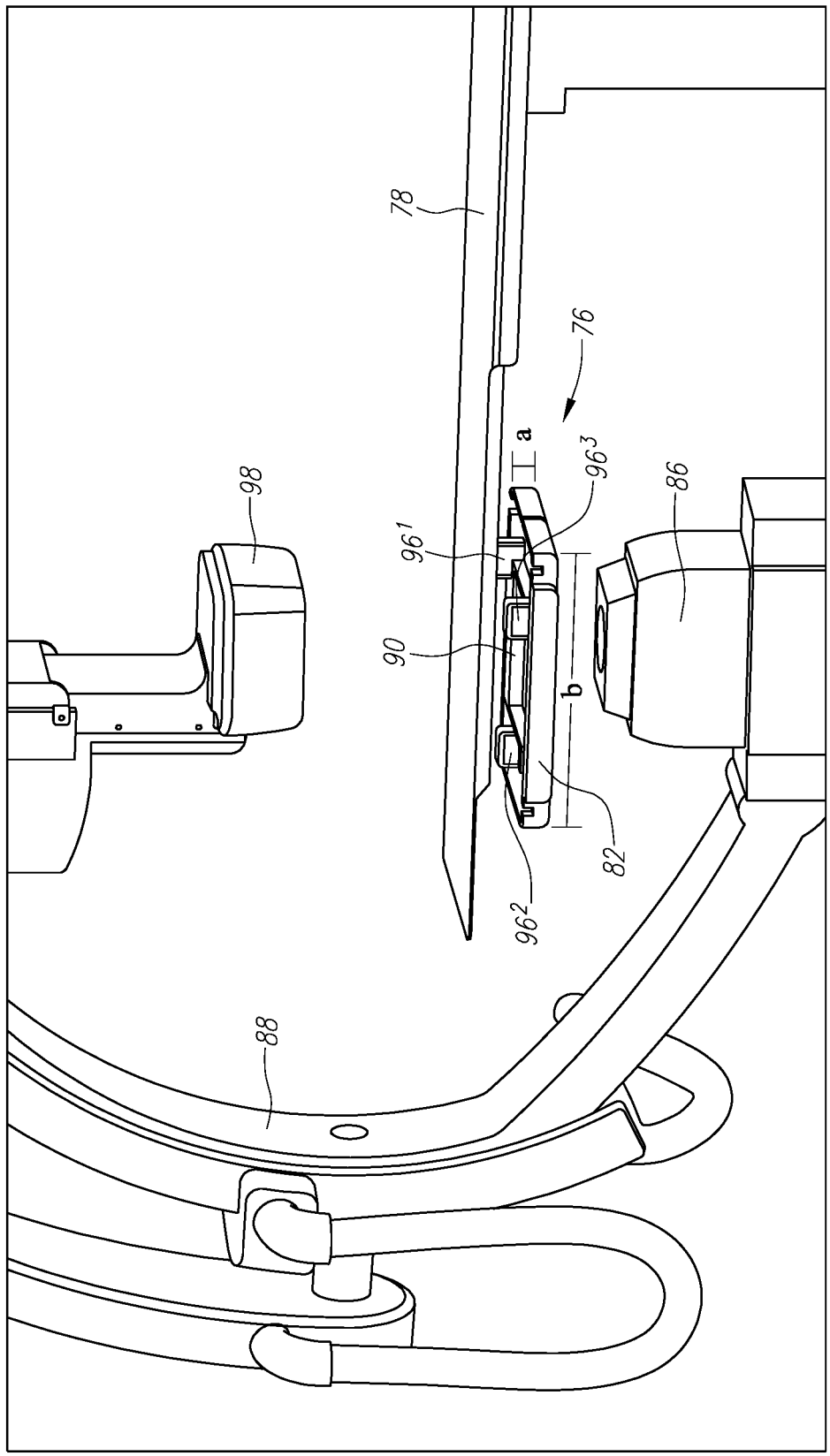

In some embodiments, asymmetric shielding can be achieved by fixing one or more layers of magnetically permeable and/or one or more layers of conductive material relative to a plurality of magnetic transmitters associated with the apparatus 36. The one or more layers can be fixed relative to the magnetic transmitters to create a predictable magnetic field of a lesser magnitude in proximity to the magnetic field-disrupting components, thus reducing a disturbance to the magnetic field located in the area of interest. The plurality of magnetic transmitters can be mounted in a plurality of different locations. In an example, the plurality of magnetic transmitters can be located in different locations relative to the asymmetric shielding, as illustrated in FIG. 5. In some examples, the plurality of magnetic transmitters can be mounted with different orientations. For example, the plurality of magnetic transmitters can be mounted at an angle with respect to the asymmetric shielding In some previous approaches, as discussed herein, an eddy current caused by the magnetic field-disrupting component can be factored out when determining a location of the catheter 12, in an example. As such, magnetic field-based systems used in previous approaches may be calibrated in order to account for magnetic field-disrupting components. For example, the disturbance caused to the magnetic field via the eddy currents can be factored out when determining a position of an object located in an area of interest. Embodiments of the present disclosure can avoid creation of eddy currents via the magnetic field-disrupting components and thus avoid calibration processes that account for magnetic field-disrupting components. This can result in a reduced installation time and an increase in ease of installation.

Figure 3:
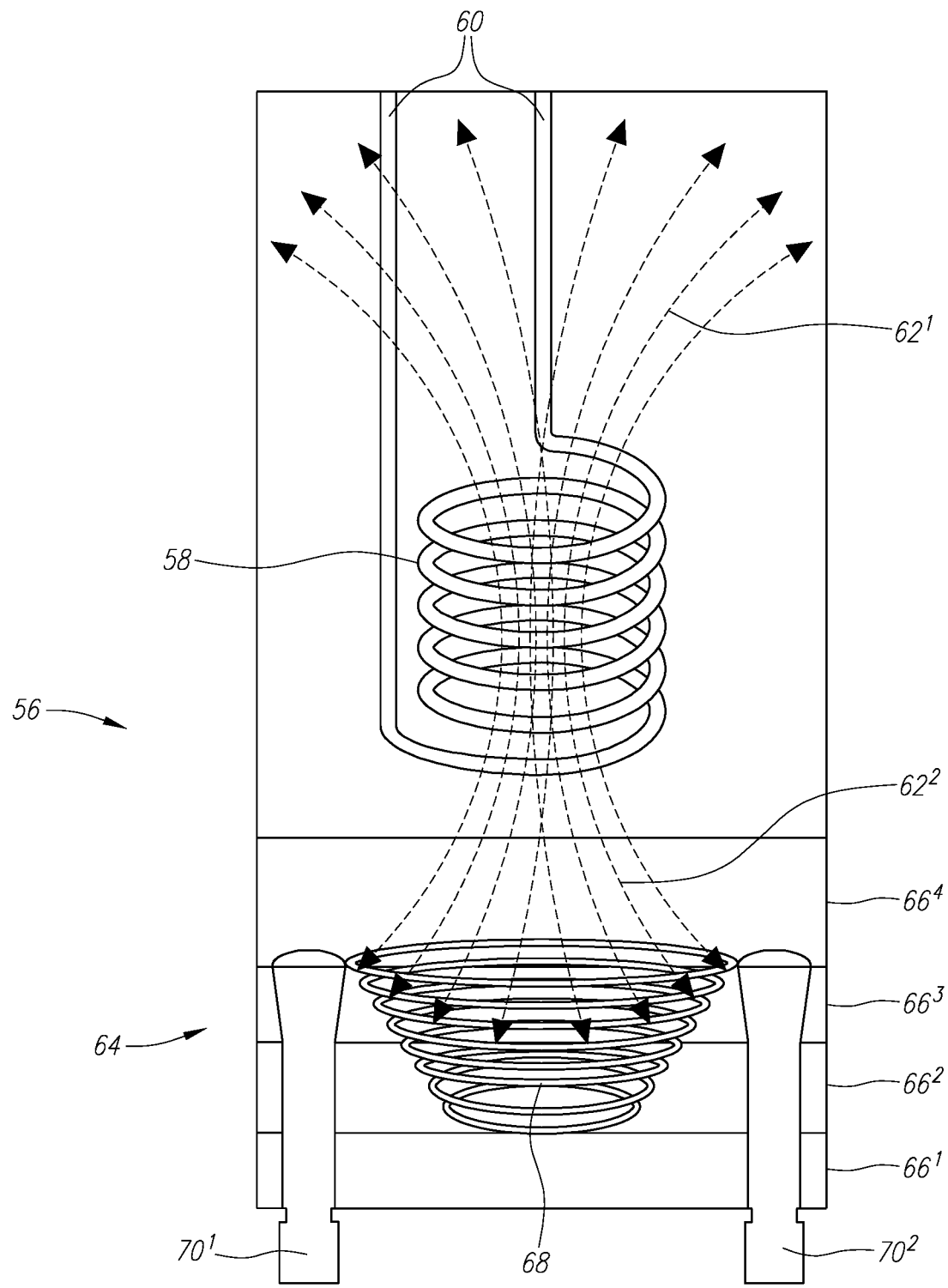
FIG. 3 depicts an apparatus for generating a magnetic field for tracking of an object, in accordance with embodiments of the present disclosure.

FIG. 3 depicts an apparatus for generating a magnetic field for tracking of an object, in accordance with embodiments of the present disclosure. In some embodiments, FIG. 3 can be illustrative of inner components of apparatus 36, in FIG. 2. The apparatus 56 can include a coil 58, which can be energized via leads 60 to produce a magnetic field $62^1$, $62^2$ that extends through a center of the coil 58 and out a top of the coil 58 and a bottom of the coil 58. In an example, magnetic field lines $62^1$ extend from a top of the coil 58 and magnetic field lines $62^2$ extend from a bottom of the coil 58. As discussed herein, in some previous approaches, magnetic field lines extending from a magnetic field generator used to produce a magnetic field for tracking of an object could be affected by magnetic field-disrupting components, such as the c-arm 42, x-ray source 40, etc. In some examples, disturbances (e.g., eddy currents) could be created in the magnetic field $62^1$, $62^2$ and cause inaccuracies in the tracking of the object.

In some embodiments of the present disclosure, the apparatus 36 can be a localized magnetic field generator that can be configured to generate the magnetic field $62^1$, $62^2$ and control the magnetic field $62^1$, $62^2$ in an area of interest and can be configured to control the magnetic field $62^1$, $62^2$ in a separate area. The area of interest 38 can include the object (e.g., catheter 12), while the separate area can be displaced from the area of interest 38 and can include a magnetic field-disrupting component. For example, as depicted in FIG. 2, the separate area can include the x-ray source 40, the c-arm 42, or another object that can disturb the magnetic field produced by the apparatus 36.

In an example, as discussed herein, the coil 58 can create the magnetic field $62^1$, $62^2$ and a magnetic field shield 64 can control the magnetic field $62^1$, $62^2$. In some examples, the magnetic field shield 64 can include one or more layers of a magnetically permeable material. As shown in FIG. 3, the magnetic field shield can include a first layer $66^1$, second layer $66^2$, third layer $66^3$, and fourth layer $66^4$, although any number of layers can be used in embodiments of the present disclosure.

In some embodiments, the various layers of the magnetic field shield 64 can be formed of magnetically permeable and/or conductive material. Magnetically permeable materials can include for example, mu-metal, iron, among other types of magnetically permeable materials. Conductive materials can include for example, aluminum, stainless steel, among other types of conductive materials. In some embodiments, the magnetically permeable and/or conductive layers can be discreet layers and/or a single layer that includes a composite of magnetically permeable and conductive materials. In some embodiments, the magnetic field shield 64 can include alternating layers of magnetically permeable and conductive materials. In some embodiments, multiple adjacent layers in the magnetic field shield 64 can be formed from magnetically permeable or conductive materials. For example, adjacent layers can be formed of a same or different type of magnetically permeable material. Alternatively, for example, adjacent layers can be formed of a same or different type of conductive material. The magnetic field shield 64 can reduce a disturbance to the magnetic field $62^1$, $62^2$ caused by the magnetic field-disrupting components. In an example, as depicted in FIG. 3, the magnetic field lines $62^2$ that extend from a bottom of the magnetic coil 58 can be drawn to and/or deflected from the magnetic field shield via a combination of magnetically permeable and/or conductive materials.

In some examples, the magnetic field $62^2$ extending from the bottom of the coil 58 can be drawn into the magnetic field shield 64 and can form eddy currents 68, as the magnetic field $62^2$ enters the various layers of the magnetic field shield 64. As the magnetic field $62^2$ travels further through the magnetic field shield 64, the eddy currents 68 can be reduced as the magnetic field $62^2$ loses energy to the magnetic field shield 64. As such, the magnetic field $62^1$, $62^2$ can be controlled by the magnetic field shield 64, preventing the magnetic field $62^1$, $62^2$ from interacting with magnetic field-disrupting components, which can reduce a disturbance to the magnetic field $62^1$, $62^2$ caused by the magnetic field-disrupting components. In some embodiments, the magnetic field $62^1$ can be projected into the area of interest 38 to provide for a magnetic navigation field in which a medical device (e.g., catheter 12) that includes magnetic position sensors can be navigated, as discussed herein. In contrast to some prior approaches, the magnetic field $62^1$ can be un-disrupted (e.g., undisturbed) by the magnetic field-disrupting components, providing for an accurate navigation of the medical device through use of the magnetic position sensors in the magnetic field $62^1$. The magnetic field shield 64 can be used in embodiments of the present disclosure in order to reduce a disturbance to the magnetic field $62^1$, $62^2$.

In some embodiments, the magnetic field shield 64 can be fastened together via fasteners $70^1$, $70^2$. In an example, the fasteners can be any kind of fasteners including pins, screws, etc. Alternatively, the layers of the magnetic field shield can be connected via other types of fastening systems including an adhesive and/or welding for example. In some examples, the layers can be stacked on top of one another without use of fasteners between each individual layer.

In some embodiments, the coil 58 can be formed of various thicknesses of wire and various numbers of windings. In some examples, as a wire thickness and various numbers of windings of the coil 58 changes, a range and/or strength of the magnetic field can change. As such, the numbers of windings of the coil 58 can be chosen to create a magnetic field $62^1$, $62^2$ that is sized such that little to no disturbance of the magnetic field $62^1$, $62^2$ is caused by the magnetic field-disrupting components. A thickness of the wire can typically vary from 3 millimeters to 10 micrometers. However, the thickness of the wire can be greater than 3 millimeters or less than 10 micrometers, in some embodiments.

Figure 4:
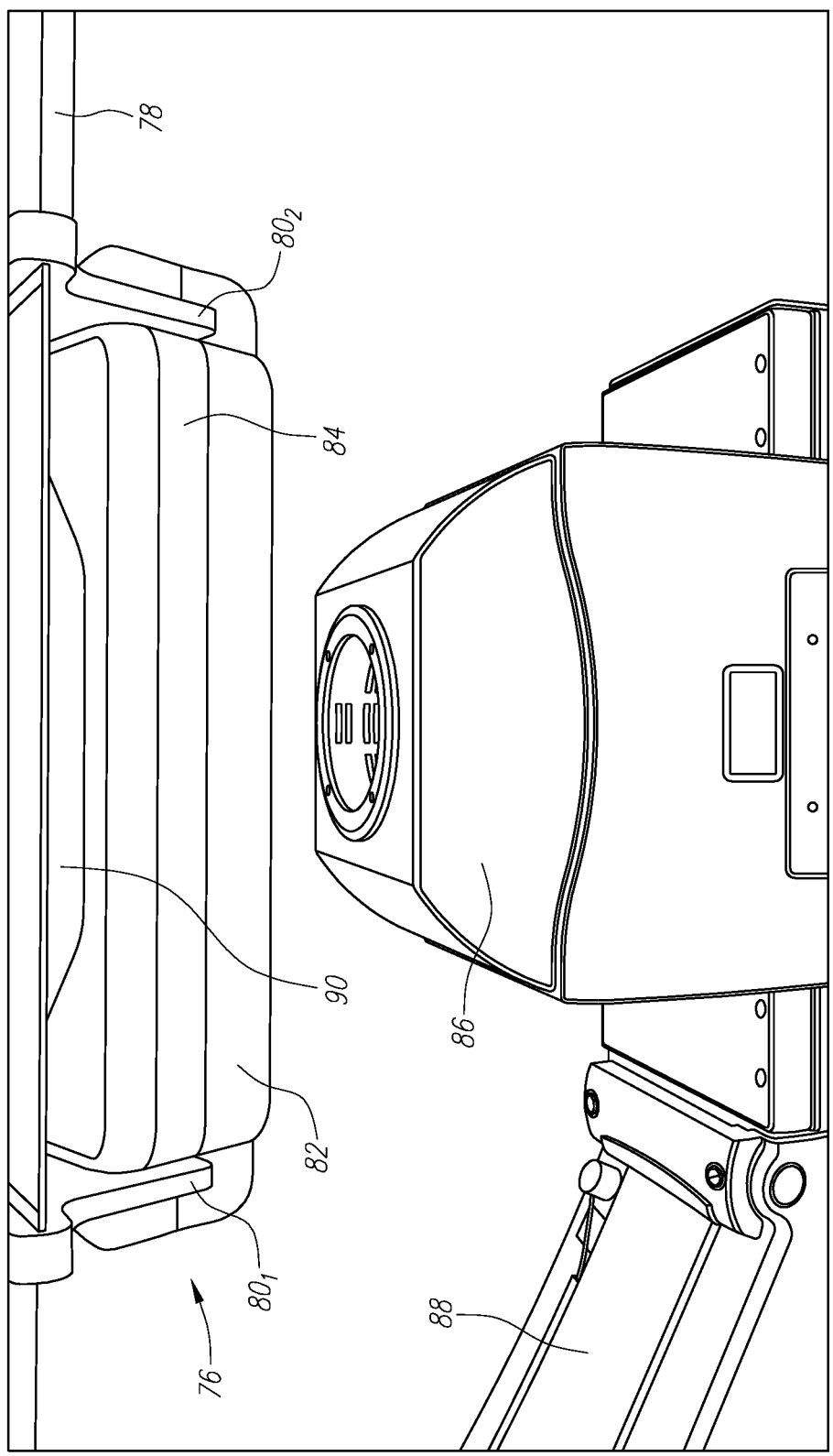
FIGS. 4 and 5 depict isometric views of the medical positioning system in FIG. 2, in accordance with embodiments of the present disclosure.

FIG. 4 depicts an isometric view of the medical positioning system in FIG. 2, in accordance with embodiments of the present disclosure. In some embodiments, the medical positioning system can include a localized magnetic field generator 76 that can be configured to generate a magnetic field and control the magnetic field in an area of interest and can be configured to control the magnetic field in a separate area.

As depicted, the localized magnetic field generator 76 can be mounted to an underside of a patient examination table 78 via mounts $80^1$, $80^2$. The localized magnetic field generator 76 can include magnetic transmitting elements (further depicted in FIGS. 5 and 6) located proximate to a magnetic field shield 82 and configured to generate the magnetic field. A cover 84 can be placed over the magnetic field shield 82, which can enclose the coils located proximate to the magnetic field shield 82. In some examples, the cover 84 can be made from a polymer, such as plastic; a composite, such as a woven fabric; and/or metal.

The magnetic field shield 82 can include a first side and second side. In some examples, a first side of the magnetic field shield 82 can face the patient examination table 78 and a plurality of magnetic transmitting elements (e.g., coils) can be located proximate to the magnetic field shield 82 and located on the first side of the magnetic field shield 82 facing the patient examination table 78. In some examples, the magnetic transmitting elements can be connected with the magnetic field shield 82 and/or mounted to a proximate structure, such that they are suspended above the first side of the magnetic field shield 82 in a stationary configuration.

In some embodiments, the magnetic field shield 82 can be located between the magnetic transmitting elements and a magnetic field-disrupting component. In an example, the magnetic field-disrupting component can be an object that has a disruptive effect on the magnetic field produced by the magnetic transmitting elements. The magnetic field-disrupting component can include an x-ray source 86, a c-arm 88, etc. In an example, the magnetic field-disrupting component can move with respect to the localized magnetic field generator. For example, the x-ray source 86 and/or c-arm 88 may be moved with respect to the magnetic field generated by the magnetic transmitting elements in the localized magnetic field generator 76. As such, it can be difficult to predict the effect that the magnetic field-disrupting components will have on the magnetic field; because their effect on the magnetic field can change as the magnetic field-disrupting components are moved with respect to the localized magnetic field generator 76 and the area of interest 38.

In some embodiments, as discussed herein, the magnetic field shield 82 can include one or more layers of magnetically permeable and/or conductive material. In an example, the magnetic field shield 82 can include at least two planar layers of material. For instance, one layer of material can be magnetically permeable and the other layer of material can be a conductive material. In some embodiments, the magnetic field shield 82 can include a first planar layer of material proximate to the patient examination table 78 and a second layer of material abutting the first planar layer of material and distal to the patient examination table 78.

In some embodiments, the plurality of magnetic transmitting elements can include at least 3 magnetic transmitting elements arranged on the first side of the magnetic field shield 82, which can be configured to direct a magnetic field in the area of interest 38. In an example, the magnetic transmitting elements can generate an asymmetric field directed perpendicular to and away from the side of the magnetic field shield 82 on which the magnetic transmitting elements are located. As such, in some embodiments, the magnetic field can be directed away from the magnetic field-disrupting components, thus avoiding formation of eddy currents in the magnetic field.

A thickness of the magnetic field shield 82 can be chosen such that a minimal amount or none of the magnetic field passes through the magnetic field shield 82. In an example, a depth of penetration of the magnetic field into the magnetic field shield 82 can be determined through the following equation:

$$\delta = \sqrt{\frac{\rho}{\pi f \mu}}$$

where ρ is defined as a resistivity of the magnetic field shield in units of Ω*m, ƒ is defined as a frequency in Hertz of the magnetic field. μ is an absolute magnetic permeability of the magnetic field shield, which is calculated through the following equation:

$$\mu = \mu_0 * \mu_r.$$

where $\mu_0$ to is equal to $4\pi*10^{-7}$ H/m.

In some embodiments, a hole 90 can be formed in the magnetic field shield 82. In some embodiments, the hole can be formed in the middle of the magnetic field shield 82 to allow for an area for x-rays to pass through from the x-ray source 86. In some embodiments, the hole can be circular, square, triangular, or another shape. The plurality of magnetic transmitting elements can be arranged around the hole 90 formed in the magnetic field shield 82, as shown further in relation to FIG. 5. The hole 90 can allow for minimal interference to the x-ray image and/or minimal occlusion of the x-ray image since the hole 90 can allow for x-rays to pass through the magnetic field shield 82 from the x-ray source.

In some embodiments of the present disclosure, a planar width, as defined by line b, of the magnetic field shield 82 can be proportional to a distance between the magnetic transmitting elements and a closest magnetic field-disrupting component. For instance, if the x-ray source 86 is a closest magnetic field-disrupting component to the magnetic transmitting elements, a distance from the magnetic field transmitting elements and/or a closest magnetic field transmitting element to the x-ray source 86 can be approximately proportional to a planar width of the magnetic field shield 82. In some examples, the magnetic field shield 82 can be at least as wide as a distance between the closest magnetic field-disrupting component and the magnetic field transmitting elements and/or the closest magnetic field transmitting element. In some embodiments, where the magnetic field shield 82 includes a lip around a perimeter of the magnetic field shield, as discussed in relation to FIGS. 5 and 6, the width of the magnetic field shield 82 can be less than the distance between the closest magnetic field-disrupting component and the magnetic field transmitting elements and/or the closest magnetic field transmitting element.

FIG. 5 depicts an alternate isometric view of the medical positioning system in FIG. 2, in accordance with embodiments of the present disclosure. As discussed herein, the medical positioning system can include a localized magnetic field generator 76. The localized magnetic field generator 76 can be located between a patient examination table 78 and a magnetic field-disrupting component (e.g., x-ray source 86, c-arm 88). The localized magnetic field generator 76 can include a magnetic field shield 82 that includes a first side and a second side. A plurality of magnetic transmitting elements $96^1, 96^2, 96^3$ can be located proximate to the magnetic field shield 82 and on the first side of the magnetic field shield 82. In some embodiments, the plurality of magnetic transmitting elements $96^1, 96^2, 96^3$ can be located between the magnetic field shield 82 and the patient examination table 78.

In some embodiments, as discussed herein, the magnetic field shield 82 can include a hole 90 through the magnetic field shield 82. In an example, the hole 90 can be located through a middle of the magnetic field shield 82, such that x-rays from the x-ray source 86 can pass through the magnetic field shield 82, through the patient examination table 78, to the image intensifier 98.

In some embodiments, as discussed herein, the magnetic transmitting elements $96^1, 96^2, 96^3$ can be mounted in different locations relative to the magnetic field shield 82. For example, the magnetic transmitting elements $96^1, 96^2, 96^3$ can be mounted around the hole 90. In some embodiments, the magnetic transmitting elements $96^1, 96^2, 96^3$ can be mounted with different orientations with respect to the magnetic field shield 82. For example, the magnetic transmitting elements $96^1, 96^2, 96^3$ can be mounted at an angle with respect to the magnetic field shield 93. In some embodiments, the magnetic transmitting elements $96^1, 96^2, 96^3$ can direct a magnetic field towards a particular point. In an example, the particular point can be inside the area of interest. In some embodiments, the magnetic transmitting elements $96^1, 96^2, 96^3$ can be mounted at a same angle with respect to the magnetic field shield 82. In addition, the magnetic transmitting element $96^1, 96^2, 96^3$ can be rotated with respect to one another. For instance, the magnetic transmitting elements $96^1, 96^2, 96^3$ can be mounted at a same angle and can be rotated with respect to one another, such that they are directed toward the opening 90 and/or area of interest 38.

In some embodiments, the magnetic field shield 82 can form a planar surface and the magnetic transmitting elements can be located proximate to the planar surface on a first side of the planar surface. In some examples, the first side of the planar surface can face the patient examination table 78 and/or the area of interest 38. In some embodiments, as discussed herein, the magnetic field shield 82 can include one or more layers of magnetically permeable and/or conductive material. In an example, the magnetic field shield 82 can include at least two planar layers of material. For instance, one layer of material can be magnetically permeable and the other layer of material can be a conductive material. In some embodiments, the magnetic field shield 82 can include a first planar layer of material proximate to the patient examination table 78 and a second layer of material abutting the first planar layer of material and distal to the patient examination table 78.

In some embodiments, the magnetic field shield 82 can include a lip formed around a perimeter of the magnetic field shield 82. The lip can be formed on a same side of the magnetic field shield 82 as the plurality of magnetic transmitting elements $96^1, 96^2, 96^3$. In an example, the lip can help shield the magnetic transmitting elements $96^1, 96^2, 96^3$ from the magnetic field-disrupting components and also help reduce a strength of the magnetic field in areas that include the magnetic field-disrupting components and/or deflect the magnetic field generated by the magnetic transmitting elements $96^1, 96^2, 96^3$ away from the areas that include the magnetic transmitting elements $96^1, 96^2, 96^3$. In some embodiments, the lip can be formed from the same one or more layers of magnetically permeable and/or conductive material that form the planar surface of the magnetic field shield. In some embodiments, the lip can be formed from a different number of layers and/or different magnetically permeable and/or conductive material than the planar surface of the magnetic field shield 82.

In some embodiments, the magnetic field shield 82 can include a lip around the hole 90 formed in the magnetic field shield 82. The lip formed around the perimeter of the magnetic field shield 82 and/or the lip formed around the perimeter of the hole 90 in the magnetic field shield 82 can generally extend perpendicularly from the planar surface of the magnetic field shield 82 in a same direction of the magnetic field shield 82 on which the magnetic transmitting elements $96^1$, $96^2$, $96^3$ are located. In an example, the lip can extend toward the area of interest 38.

In some embodiments, a length, as defined by line a, between the planar surface of the magnetic field shield 82 and a top of the lip can be in a range of 0.1 to 2.0 times a distance between the planar surface and a top of the magnetic transmitting elements $96^1$, $96^2$, $96^3$. As such, the magnetic field shield 82 can form a dish in which the magnetic transmitting elements $96^1$, $96^2$, $96^3$ are mounted in. This can help shield the magnetic transmitting elements $96^1$, $96^2$, $96^3$ from magnetic field-disrupting components; help contain the magnetic field produced by the magnetic transmitting elements $96^1$, $96^2$, $96^3$; and/or help deflect the magnetic field produced by the magnetic transmitting elements $96^1$, $96^2$, $96^3$ from the magnetic field-disrupting components.

Figure 6:
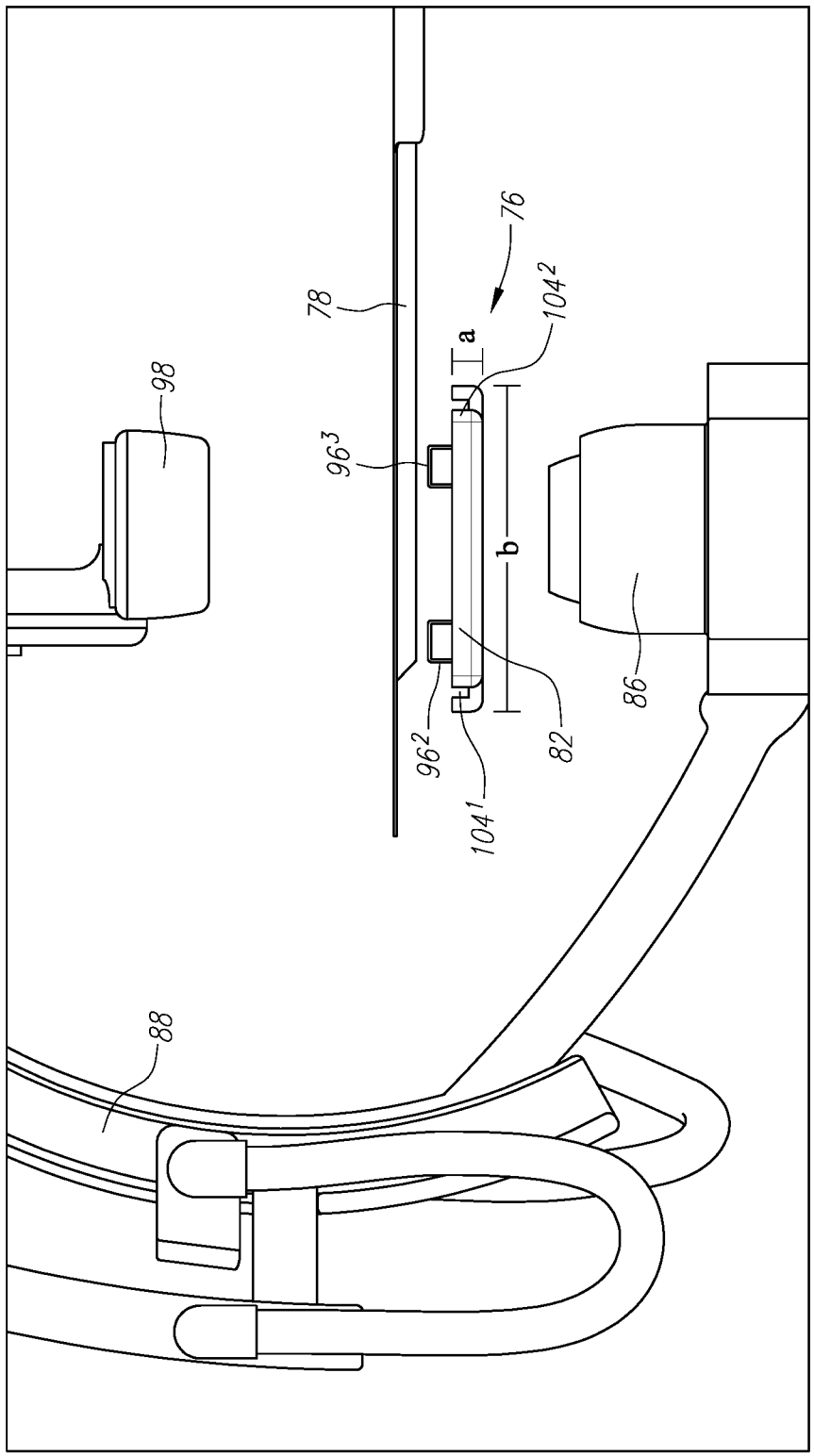
FIG. 6 depicts a side view of the medical positioning system in FIG. 2, in accordance with embodiments of the present disclosure.

FIG. 6 depicts a side view of the medical positioning system in FIG. 2, in accordance with embodiments of the present disclosure. As discussed herein, the medical positioning system can include a localized magnetic field generator 76. The localized magnetic field generator 76 can be located between a patient examination table 78 and a magnetic field-disrupting component (e.g., x-ray source 86, c-arm 88). The localized magnetic field generator 76 can include a magnetic field shield 82 that includes a first side and a second side. A plurality of magnetic transmitting elements $96^1$, $96^2$ (obscured in FIG. 6 by magnetic transmitting element $96^3$), $96^3$ can be located proximate to the magnetic field shield 82 and on the first side of the magnetic field shield 82. In some embodiments, the plurality of magnetic transmitting elements $96^1$, $96^2$, $96^3$ can be located between the magnetic field shield 82 and the patient examination table 78.

As discussed in relation to FIG. 5, the magnetic field shield 82 can include a hole positioned above the x-ray source 86 to allow for x-rays to pass through the magnetic field shield 82 to the image intensifier 98. In some embodiments, the magnetic field shield 82 can include mounting slots $104^1$, $104^2$, which can be configured for connecting the magnetic field shield 82 with the patient examination table 78 via mounts $80^1$, $80^2$.

In some embodiments of the present disclosure, the magnetic field produced by the magnetic transmitting elements $96^1$, $96^2$, $96^3$ can be further shaped through use of a plurality of synchronized magnetic transmitting elements to create a phased array of magnetic transmitting elements. In an example, a plurality of synchronized transmitting elements can be grouped together and act as a single transmitting element (e.g., transmitting element $96^1$) and produce a magnetic field at a same frequency. Additional transmitting elements can be grouped together and act as different magnetic transmitting elements that produce a second, third, etc. magnetic field at different frequencies with respect to the single transmitting element and with respect to one another. As such, through use of a plurality of synchronized magnetic transmitting elements, a synchronized magnetic field transmission can be produced to shape the magnetic field.

In some embodiments, a Halbach array, and/or a Helmholtz coil can be used to shape the magnetic field produced by the magnetic transmitting elements. In some embodiments, a Halbach array can augment a magnetic field on a first side of the array and cancel out a magnetic field on an opposite side of the array to a near zero value. As such, the magnetic field on the first side can be directed to an area of interest, and a negligible magnetic field can be produced on the opposite side of the Halbach array, which interacts minimally with magnetic field-disrupting components or does not interact at all with the magnetic field-disrupting components. As such, a magnetic field shield may not be used with the Halbach array. In some embodiments, a Helmoltz coil can be used to shape the magnetic field produced by the magnetic transmitting elements. In an example, a pair of coils can be placed on either side of the area of interest and a uniform or near uniform magnetic field can be produced between the coils.

Figure 7:
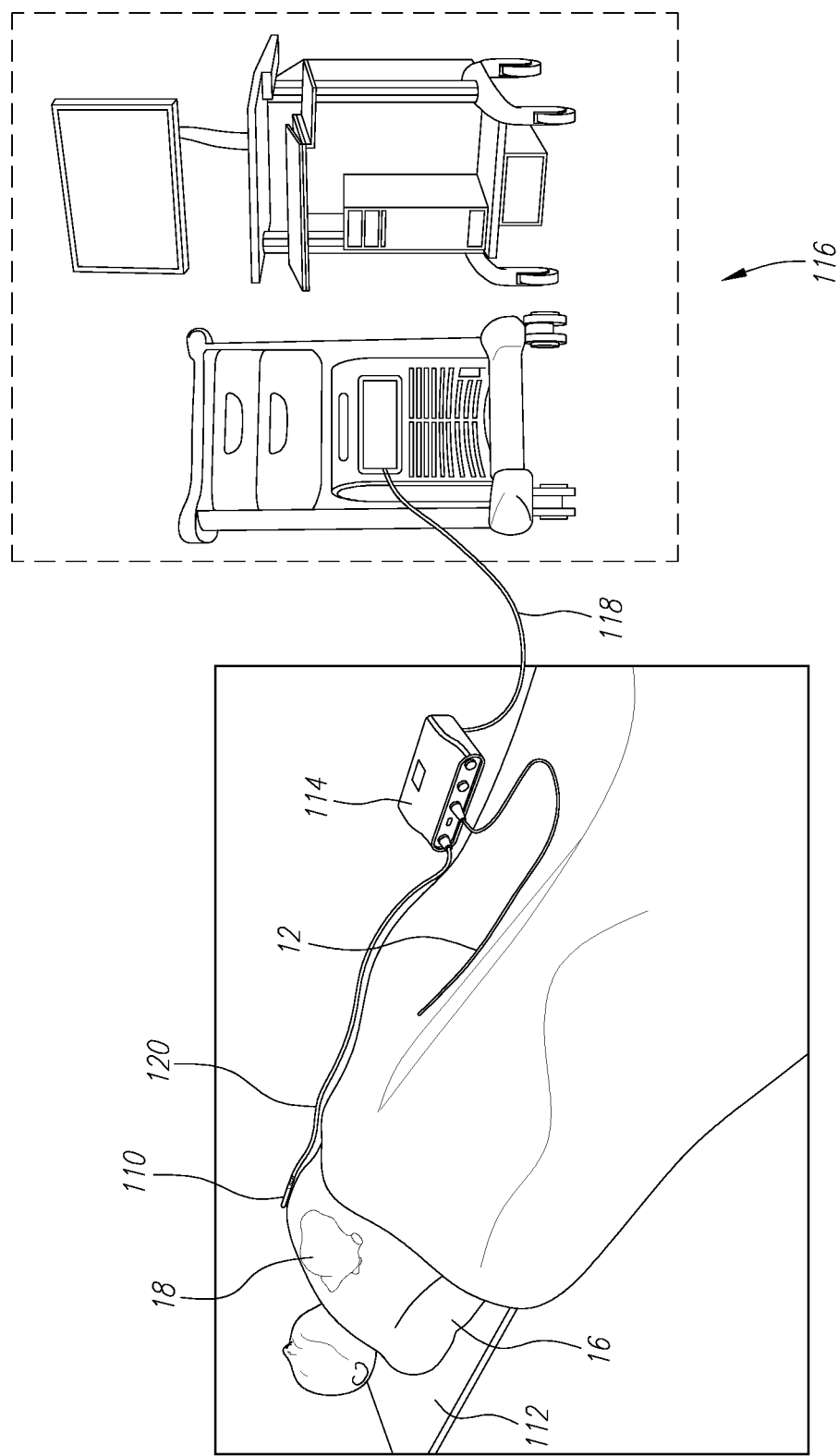
FIG. 7 depicts a mobile medical positioning system, in accordance with embodiments of the present disclosure.

FIG. 7 depicts a mobile medical positioning system, in accordance with embodiments of the present disclosure. The mobile medical positioning system can include a mobile localized magnetic field generator 110 that can be placed proximate to a heart 18 of the patient 16. In an example, the mobile localized magnetic field generator 110 can be placed on a chest of the patient 116, on a side of the patient, on a back of the patient, etc. In an example, when the mobile localized magnetic field generator 110 is placed on the back of the patient 116, the mobile localized magnetic field generator 110 can be placed between the patient examination table 112 and the patient 116.

The mobile medical positioning system 110 can generate a magnetic field and control the magnetic field in an area of interest and can control the magnetic field in a separate area. In some embodiments, as discussed herein, the area of interest can include an object (e.g., catheter 12), which can be inserted into the patient 16 heart 18. The separate area can be displaced from the area of interest 38 and can include a magnetic field-disrupting component. For example, the separate area can include an x-ray source, c-arm, or another object, as depicted in FIG. 2, that can disturb the magnetic field produced by the mobile localized magnetic field generator 110.

In some embodiments, the mobile localized magnetic field generator 110 can generate a localized magnetic field in the area of interest, which can be detected by a sensor included in the catheter 12. The mobile localized magnetic field generator 110 can be coupled to a controller 114 via a cable 120, which can provide power to the mobile localized magnetic field generator 110 and can control the mobile localized magnetic field generator 110. The sensor can be configured to detect one or more characteristics of the magnetic field, which can be used to determine a three-dimensional position and/or orientation reading for the sensor. The sensor can be coupled to a controller 114 with a sensor cable, which can provide electrical signals to the controller for determination of the three-dimensional position and/or orientation reading. The controller can be coupled via a cable 118 to a mapping system 116. In some embodiments, the cable 118 can have magnetic shielding around a core of the cable to prevent interference from magnetic field-disrupting components. The mapping system can process the electrical signals received from the controller 114 to determine the three-dimensional position and/or orientation reading.

Some embodiments of the present disclosure can be compatible with cardiac mapping systems such as, for example, an Ensite Velocity™ cardiac mapping system. In some examples, the mobile localized magnetic field generator 110 can be coupled to the cardiac mapping system via cables 118, 120 and the controller 114.

Figure 8:
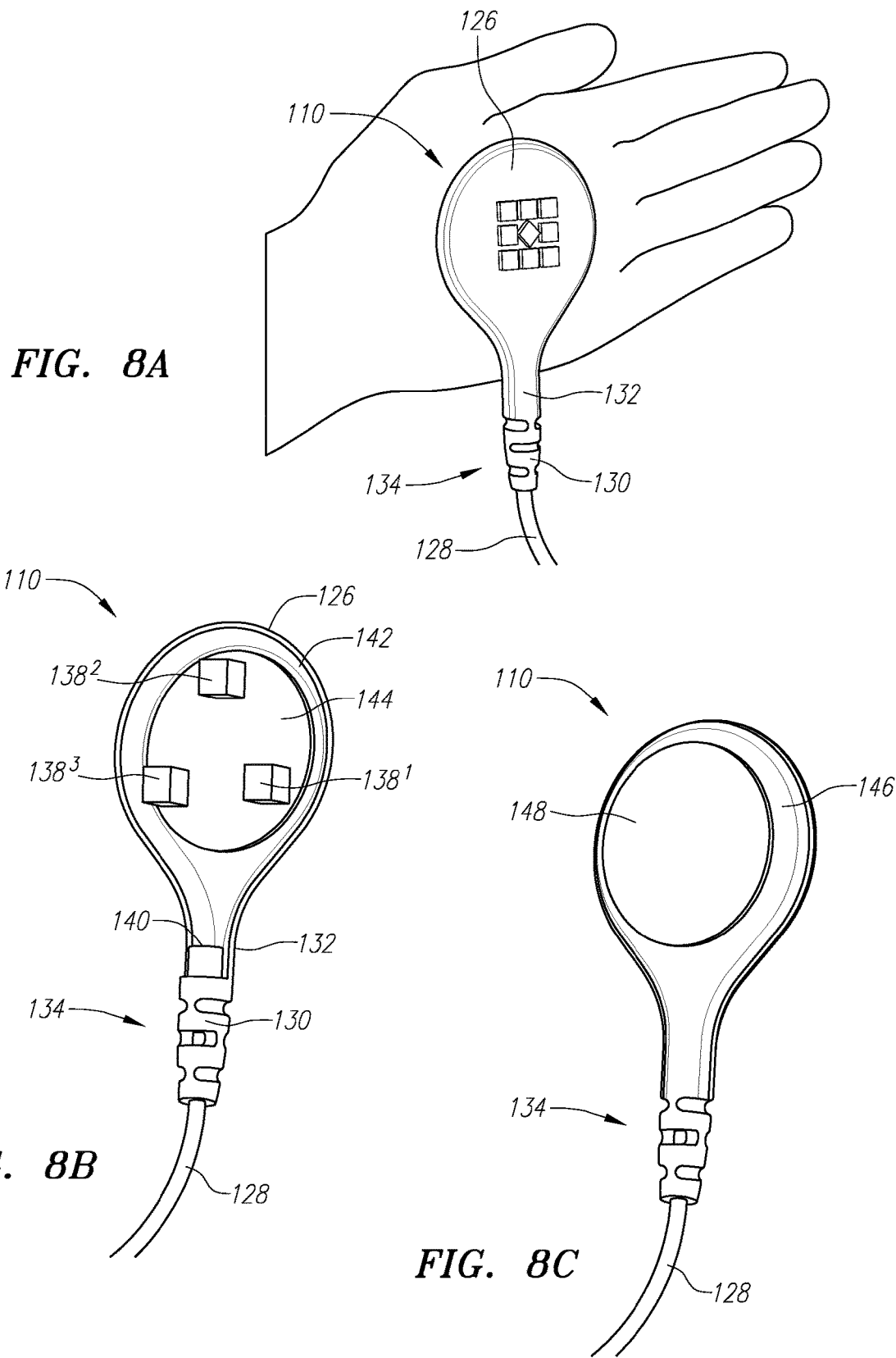
FIG. 8A depicts a back view of the mobile localized magnetic field generator in FIG. 7, in accordance with embodiments of the present disclosure.
FIG. 8B depicts an internal front view of the mobile localized magnetic field generator in FIG. 7, in accordance with embodiments of the present disclosure.
FIG. 8C depicts a front view of the mobile localized magnetic field generator in FIG. 7, in accordance with embodiments of the present disclosure.

FIG. 8A depicts a back view of the mobile localized magnetic field generator in FIG. 7, in accordance with embodiments of the present disclosure. The mobile localized magnetic field generator 110 can include a back plate 126. The back plate 126 can be directed away from the area of interest when the mobile localized magnetic field generator 110 is positioned proximate to the area of interest. In an example, the back plate 126 can be configured to control the magnetic field in the area of interest and configured to control the magnetic field in a separate area. In an example, a magnetic field shield, as discussed herein, can be connected with the back plate 126 and/or can be integral with the back plate 126. The magnetic field shield can be formed of magnetically permeable and/or conductive material and can be configured to direct a magnetic field generated by the mobile localized magnetic field generator 110 toward the area of interest and/or away from the separate area that includes the magnetic field-disrupting components.

The mobile localized magnetic field generator 110 can include a wire mount portion 134, that can be configured for connecting a wire 128 with the back plate 126 and/or mobile localized magnetic field generator 110. In some embodiments, the wire mount portion 134 can include a rigid portion 132 and a flexible portion 130. The flexible portion 130 can prevent the wire 128 from flexing at one point, thus increasing a distance over which the wire bends and reducing a chance that the wire 128 will fray or break. In some embodiments, the rigid portion 132 can be used to hold and/or position the mobile localized magnetic field generator 110. In some embodiments, the back plate 126, the rigid portion 132, and the flexible portion 130 can be formed from a single piece of material. Alternatively, the back plate 126, the rigid portion 132, and/or the flexible portion 130 can be formed from separate pieces of material and can be connected with one another.

FIG. 8B depicts an internal front view of the mobile localized magnetic field generator in FIG. 7, in accordance with embodiments of the present disclosure. In an example, a front plate has been removed from the mobile localized magnetic field generator. The mobile localized magnetic field generator 110 can be tear drop shaped in some embodiments, as depicted in FIG. 8A, 8B, 8C. However, the mobile localized magnetic field generator 110 can be formed as a square, triangle, rectangle, etc. In some embodiments, the mobile localized magnetic field generator 110 may not include mounts configured to mount the mobile localized magnetic field generator 110 to a stationary object (e.g., e.g., patient examination table 46). For example, the magnetic field generator 110 can be a handheld device and can be configured to be placed directly on a patient (e.g., patient's chest).

The mobile localized magnetic field generator 110 can include the back plate 126, which can be connected with and/or can be integral with a magnetic field shield 142. The magnetic field shield 142 can include those features, as discussed in the present disclosure. As discussed herein, the magnetic field shield 142 can be formed from a magnetically permeable and/or a conductive material. In some embodiments, the magnetic field shield 142 can include one or more layers of a magnetically permeable material. As discussed herein, the magnetic field shield 142 can include a first layer, second layer, third layer, and fourth layer, although any number of layers can be used in embodiments of the present disclosure.

The magnetic field shield 142 can be circular in shape, as shown in FIG. 8B. In some embodiments, the magnetic field shield 142 can be formed as a square, rectangle, triangle, among other shapes. The magnetic field shield 142 can typically have a thickness in a range from a thickness that is equivalent to a thickness and/or height of magnetic transmitting elements $138^1$, $138^2$, $138^3$ to a thickness that is 100 times smaller than a thickness and/or height of magnetic transmitting elements $138^1$, $138^2$, $138^3$. In some embodiments, the magnetic field shield 142 can have a width that is in a range from a width that is equivalent to a width of the magnetic transmitting elements $138^1$, $138^2$, $138^3$ to a width that is 100 times larger than the width of the magnetic transmitting elements $138^1$, $138^2$, $138^3$. In some embodiments, the magnetic field shield 142 can have an area that is in a range from an area that is equivalent to an area of the magnetic transmitting elements $138^1$, $138^2$, $138^3$ to an area that is 100 times larger than the area of the magnetic transmitting elements $138^1$, $138^2$, $138^3$.

In some embodiments, the magnetic field shield 142 can have a first side and a second side. The first side can be a side that is configured to face a patient and/or area of interest and the second side can be configured to face a separate area, in some embodiments. The first side can form a planar surface that faces toward the area of interest and away from the back plate 126. Magnetic transmitting elements $138^1$, $138^2$, $138^3$ can be located proximate to the first side of the magnetic field shield 142. In some embodiments, the magnetic transmitting elements $138^1$, $138^2$, $138^3$ can be connected with the first side of the magnetic field shield 142 and can face the area of interest 38. Alternatively, the magnetic transmitting elements $138^1$, $138^2$, $138^3$ can be connected with a backing 144 that, in some embodiments, can include capacitors configured to provide power to the magnetic transmitting elements $138^1$, $138^2$, $138^3$. In some embodiments, the backing 144 can be a triangular, square, rectangular, circular disc etc. The magnetic transmitting elements $138^1$, $138^2$, $138^3$ can be of a smaller size than those discussed in relation to embodiments depicted in FIGS. 4, 5, and 6. For example, the magnetic transmitting elements $138^1$, $138^2$, $138^3$ can be smaller magnetic transmitting elements $138^1$, $138^2$, $138^3$ that include smaller coils than those embodiments depicted in FIGS. 4, 5, and 6. In some embodiments, the magnetic transmitting elements $138^1$, $138^2$, $138^3$ can generate a smaller magnetic field than the magnetic transmitting elements discussed in relation to FIGS. 4, 5, and 6. Because the mobile localized magnetic field generator 110 can be configured to be placed directly on the patient 16, a smaller distance can exist between one or more magnetic sensors connected with a catheter shaft being inserted into the patient and the mobile localized magnetic field generator 110. As such, because the mobile localized magnetic field generator 110 is located closer to the one or more sensors, a magnetic field with a lesser strength can be used, while still allowing for the one or more magnetic sensors to detect characteristics of the magnetic field. In addition, use of the magnetic field with the lesser strength can be beneficial because the magnetic field of lesser strength may interact with the magnetic field-disrupting components to a lesser extent. For example, while the mobile localized magnetic field generator 110 can provide a magnetic field that is of a sufficient strength within the area of interest, the magnetic field may be of a strength in the separate area such that it does not interact with magnetic field-disrupting components.

In some embodiments, the cable 128 can extend into the flexible portion 130 and/or the rigid portion 132. The rigid portion 132 can contain an opening through which wires included in the cable 128 can pass. The wires can provide power to each of the magnetic transmitting elements $138^1$, $138^2$, $138^3$ from the controller 114.

In some embodiments, a lip can be formed around a perimeter of the magnetic field shield 142, as discussed herein. The lip can be formed on a same side of the magnetic field shield 142 as the magnetic transmitting elements $138^1$, $138^2$, $138^3$. In an example, the lip can help shield the magnetic transmitting elements $138^1$, $138^2$, $138^3$ from the magnetic field-disrupting components. In addition, the lip can help reduce a strength of the magnetic field in areas that include the magnetic field-disrupting components and/or deflect the magnetic field generated by the magnetic transmitting elements $138^1$, $138^2$, $138^3$ away from the areas that include the magnetic transmitting elements $138^1$, $138^2$, $138^3$.

As discussed herein, in some embodiments of the present disclosure, the magnetic field produced by the magnetic transmitting elements $138^1$, $138^2$, $138^3$ can be further shaped through use of a plurality of synchronized magnetic transmitting elements to create a phased array of magnetic transmitting elements. In an example, a plurality of synchronized transmitting elements can be grouped together and act as a single transmitting element (e.g., transmitting element $138^1$) and produce a magnetic field at a same frequency. Additional transmitting elements can be grouped together and act as different magnetic transmitting elements that produce a second, third, etc. magnetic field at different frequencies with respect to the single transmitting element and with respect to one another. As such, through use of a plurality of synchronized magnetic transmitting elements, a synchronized magnetic field transmission can be produced to shape the magnetic field. In some embodiments, a Halbach array, and/or a Helmholtz coil can be used to shape the magnetic field produced by the magnetic transmitting elements, as discussed herein.

FIG. 8C depicts a front view of the mobile localized magnetic field generator in FIG. 7, in accordance with embodiments of the present disclosure. The mobile localized magnetic field generator can include the wire mount portion 134 for connection of wire 128. The mobile localized magnetic field generator 110 can include a front plate 146. The front plate can be configured to connect with the back plate via an adhesive and/or type of mechanical fastener. In some embodiments, the magnetic field shield and the magnetic transmitting elements $138^1$, $138^2$, $138^1$ can be enclosed by the back plate 126 and the front plate 146.

The front plate 146 can include a pad 148, in some embodiments. The pad 148 can be a same or similar size and/or shape as the mobile localized magnetic field generator 110. The pad 148 can be connected with the front plate 146 and can be located between the patient 16 and the mobile localized magnetic field generator 110. In some examples, the mobile localized magnetic field generator 110 can include the pad 148 to improve a comfort of the patient 16. Alternatively, and/or in addition, the pad 148 can improve a connection between the mobile localized magnetic field generator 110 and the patient's body. For example, a contact gel can be placed between the pad 148 and the patient 16.

The pad 148 can be formed from a non-conductive material, in some embodiments. By forming the pad from a non-conductive material, interference with the magnetic field produced by the mobile localized magnetic field generator 110 can be avoided. In some embodiments, a hole can be formed in the front plate 146 and the pad 148 can have a channel surrounding a perimeter of the pad 148, such that the pad 148 is configured to be inserted into the hole and held in place via the channel. In some embodiments, the pad 148 can be connected with the front plate 146 via an adhesive and/or other type of fastener (e.g., screw, pin, etc.).

In some embodiments, a size of the mobile localized magnetic field generator 110 can allow for minimal interference to an x-ray image and/or minimal occlusion of an x-ray image taken of a patient. For example, an x-ray image taken of the patient may not be obscured by the mobile localized magnetic field generator 110, since a small percentage of x-rays passing through a patient 16 interact with the mobile localized magnetic field generator 110, due to its small size.

Figure 9:
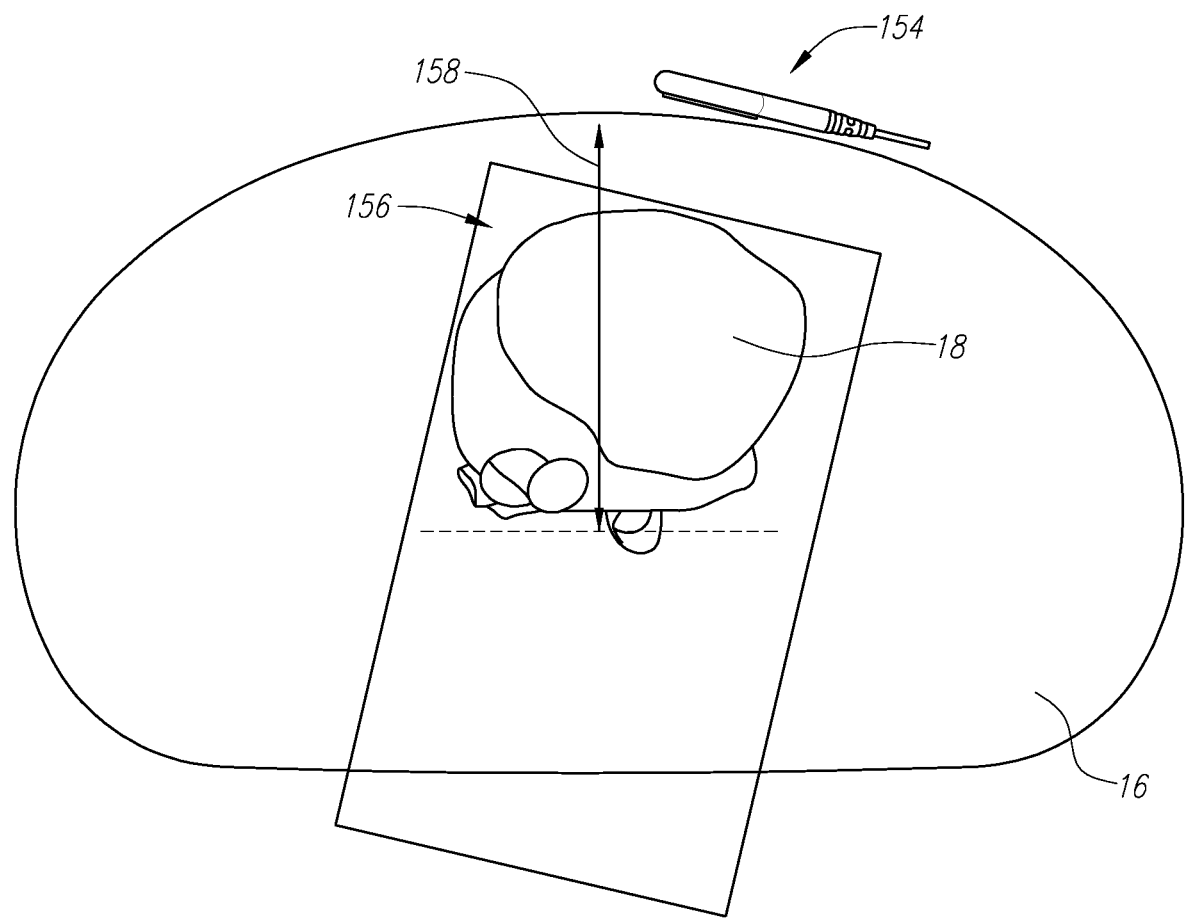
FIG. 9 depicts a motion box generated by a mobile localized magnetic field generator placed on a patient chest, in accordance with embodiments of the present disclosure.

FIG. 9 depicts a motion box generated by a mobile localized magnetic field generator placed on a patient chest, in accordance with embodiments of the present disclosure. In some embodiments, the mobile localized magnetic field generator 154 can be placed on a chest of the patient 16. In an example, the heart 18 and/or area of interest 38 can be located a particular distance away from the mobile localized magnetic field generator 154 when the mobile localized magnetic field generator 154 is placed on the chest of the patient 16. The mobile localized magnetic field generator 154 can create a magnetic field that defines a motion box 156, where movement of sensors 28 associated with the catheter 12 can be monitored. In an example, the motion box 156 can include the heart 18. In some embodiments, it can be desirable to have a motion box 156 that is inclusive of the heart 18 and/or area of interest 38 and exclusive of a separate area that includes magnetic field-disrupting components. As such, the mobile localized magnetic field generator 154 can be designed accordingly. For instance, where the localized magnetic field generator 154 is placed on the chest, a particular size of coil can be used in the mobile localized magnetic field generator 154 and/or a particular type of magnetic field shield can be used in the mobile localized magnetic field generator 154. A dimension of the magnetic field generator 154 between the first side that faces the chest of the patient 16 and the second side that faces away from the chest of the patient 16 can be between 0.2 centimeters to 5 centimeters, however, in some embodiments, the dimension can be less than 0.2 centimeters or greater than 5 centimeters. The magnetic transmitting elements can be strong enough to generate a magnetic field at a distance of between 5 and 20 centimeters. In some embodiments, the magnetic transmitting elements can be strong enough to generate a magnetic field at a distance of 13 centimeters. In some embodiments, the magnetic transmitting elements can be strong enough to generate a magnetic field along line 158. As discussed herein, the magnetic field generator 154 can also have a magnetic field shield that reduces a magnetic field in an area of the x-ray detector, which can typically be located 5 centimeters to 20 centimeters from the chest of the patient 16 and/or the magnetic field generator. In an example, the magnetic field shield can include layers of conductive and/or magnetically permeable material in a particular pattern. In some embodiments, the magnetic field shield can include a lip, as discussed herein.

In some examples, when the mobile localized magnetic field generator 154 is placed on the chest of the patient 16, the motion box 156 can be a cylinder with a diameter of approximately 15 centimeters that begins approximately 4 centimeters away from the mobile localized magnetic field generator 154 and extends to a distance (represented by line 158) of approximately 14 centimeters away from the mobile localized magnetic field generator 154. As such, the motion box 156 can have a height of approximately 8 to 10 centimeters. However, such dimensions of the motion box 156 are not inclusive and the motion box 156 can have dimensions that are larger or smaller than those discussed herein.

Figure 10:
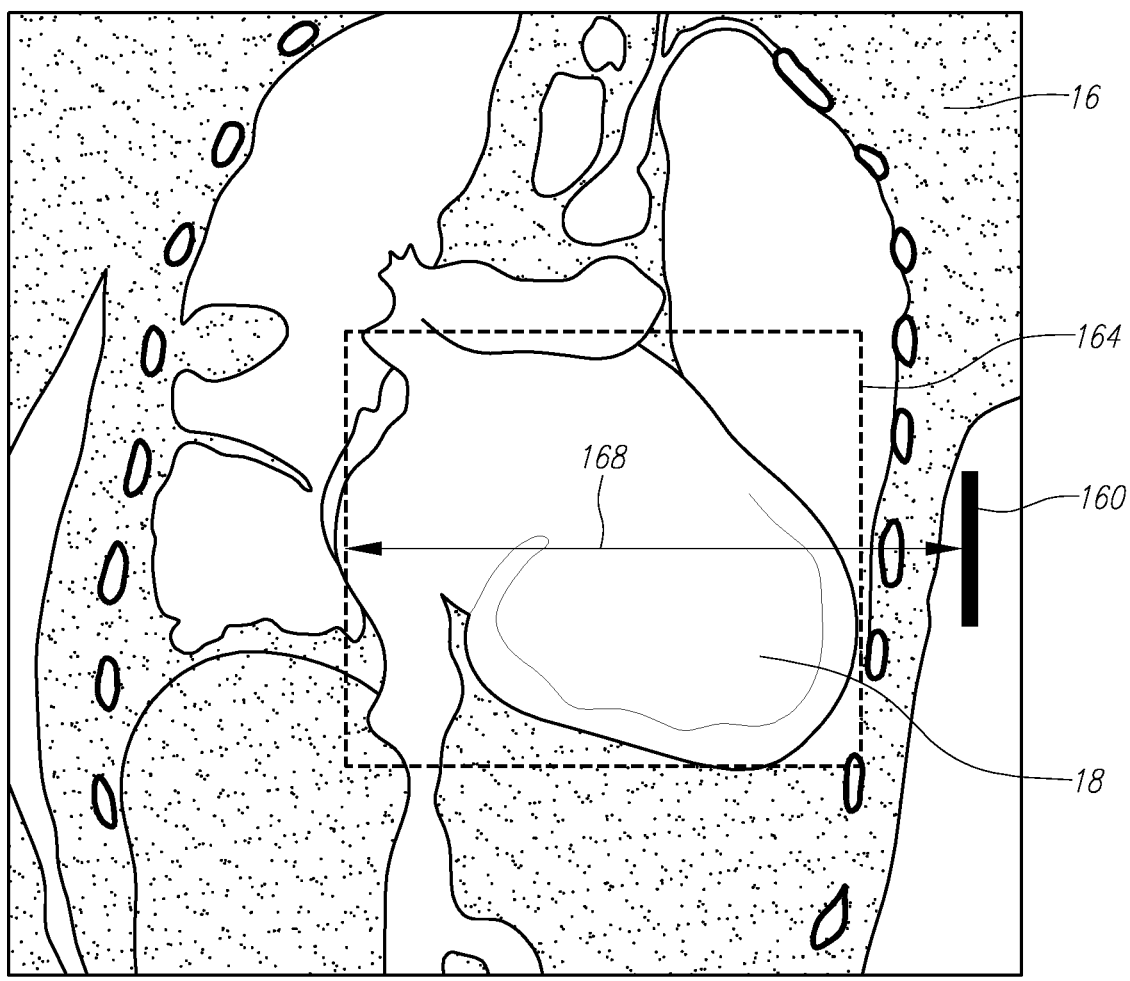
FIG. 10 depicts a motion box generated by a mobile localized magnetic field generator placed on a side of a patient, in accordance with embodiments of the present disclosure.

FIG. 10 depicts a motion box generated by a mobile localized magnetic field generator placed on a side of a patient, in accordance with embodiments of the present disclosure. In some embodiments, the mobile localized magnetic field generator 160 can be placed on a side of a chest of the patient 16. In an example, the heart 18 and/or area of interest 38 can be located a particular distance away from the mobile localized magnetic field generator 160 when the mobile localized magnetic field generator 160 is placed on the side of the chest of the patient 16. The mobile localized magnetic field generator 160 can create a magnetic field that defines a motion box 164, where movement of sensors 28 associated with the catheter 12 can be monitored. In an example, the motion box 164 can include the heart 18. As discussed herein, in some embodiments, it can be desirable to have a motion box 164 that is inclusive of the heart 18 and/or area of interest 38 and exclusive of a separate area that includes magnetic field-disrupting components. As such, a particular size of a coil used in the mobile localized magnetic field generator 160 and/or a particular type of magnetic field shield used in the mobile localized magnetic field generator 160 can be varied in the design of the mobile localized magnetic field generator 160. A dimension of the magnetic field generator 160 between the first side that faces the chest of the patient 16 and the second side that faces away from the chest of the patient 16 can be between 0.2 centimeters to 5 centimeters, however, in some embodiments, the dimension can be less than 0.2 centimeters or greater than 5 centimeters. The magnetic transmitting elements can be strong enough to generate a magnetic field at a distance of between 15 to 35 centimeters. In some embodiments, the magnetic transmitting elements can be strong enough to generate a magnetic field at a distance of approximately 25 centimeters. In some embodiments, the magnetic transmitting elements can be strong enough to generate a magnetic field along line 168. As discussed herein, the magnetic field generator 160 can also have a magnetic field shield that reduces a magnetic field in an area of the x-ray detector, which can typically be located 10 centimeters to 30 centimeters from the chest of the patient 16 and/or the magnetic field generator 160.

In some examples, when the mobile localized magnetic field generator 160 is placed on the chest of the patient 16, the motion box 164 can be a cylinder with a diameter of approximately 15 centimeters that begins approximately 4 centimeters away from the mobile localized magnetic field generator 160 and extends to a distance (represented by line 168) of approximately 26 centimeters away from the mobile localized magnetic field generator 160. As such, the motion box 164 can have a height of approximately 22 centimeters. However, such dimensions of the motion box 164 are not inclusive and the motion box 164 can have dimensions that are larger or smaller than those discussed herein.

Figure 11:
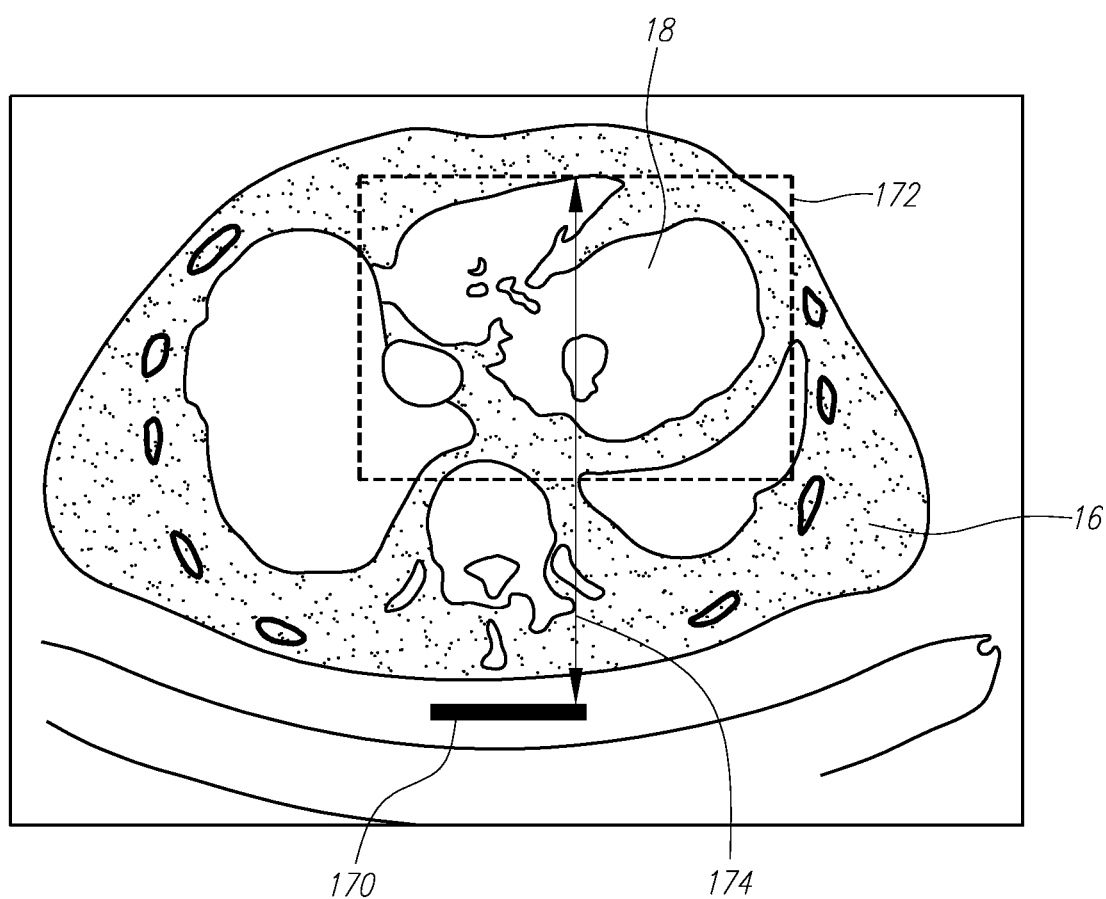
FIG. 11 depicts a motion box generated by a mobile localized magnetic field generator placed on a patient's back, in accordance with embodiments of the present disclosure.

FIG. 11 depicts a motion box generated by a mobile localized magnetic field generator placed on a patient's back, in accordance with embodiments of the present disclosure. In some embodiments, the mobile localized magnetic field generator 170 can be placed on a back of the patient 16, between the patient examination table and the patient 16. In an example, the heart 18 and/or area of interest 38 can be located a particular distance away from the mobile localized magnetic field generator 170 when the mobile localized magnetic field generator 170 is placed on the back of the patient 16. The mobile localized magnetic field generator 170 can create a magnetic field that defines a motion box 172, where movement of sensors 28 associated with the catheter 12 can be monitored. In an example, the motion box 172 can include the heart 18. As discussed herein, in some embodiments, it can be desirable to have a motion box 172 that is inclusive of the heart 18 and/or area of interest 38 and exclusive of a separate area that includes magnetic field-disrupting components. As such, a particular size of a coil used in the mobile localized magnetic field generator 170 and/or a particular type of magnetic field shield used in the mobile localized magnetic field generator 170 can be varied in the design of the mobile localized magnetic field generator 170. A dimension of the magnetic field generator 170 between the first side that faces the chest of the patient 16 and the second side that faces away from the chest of the patient 16 can be between 0.2 centimeters to 5 centimeters, however, in some embodiments, the dimension can be less than 0.2 centimeters or greater than 5 centimeters. The magnetic transmitting elements can be strong enough to generate a magnetic field at a distance of between 15 to 35 centimeters. In some embodiments, the magnetic transmitting elements can be strong enough to generate a magnetic field at a distance of approximately 25 centimeters. In some embodiments, the magnetic transmitting elements can be strong enough to generate a magnetic field along line 174. As discussed herein, the magnetic field generator 170 can also have a magnetic field shield that reduces a magnetic field in an area of the x-ray detector, which can typically be located 20 centimeters to 50 centimeters from the chest of the patient 16 and/or the magnetic field generator 170.

In some examples, when the mobile localized magnetic field generator 170 is placed on the chest of the patient 16, the motion box 172 can be a cylinder with a diameter of approximately 15 centimeters that begins approximately 4 centimeters away from the mobile localized magnetic field generator 170 and extends to a distance (represented by line 174) of approximately 26 centimeters away from the mobile localized magnetic field generator 170. As such, the motion box 172 can have a height of approximately 22 centimeters. However, such dimensions of the motion box 172 are not inclusive and the motion box 172 can have dimensions that are larger or smaller than those discussed herein.

In some embodiments where a localized magnetic field generator, such as that discussed in relation to FIGS. 4, 5, and 6, is mounted underneath a patient examination table, the heart and/or area of interest 38 can be located a particular distance away from the localized magnetic field generator. Accordingly, as discussed in relation to FIGS. 9, 10, and 11, a particular size of a coil used in the mobile localized magnetic field generator and/or a particular type of magnetic field shield used in the mobile localized magnetic field generator can be varied in the design of the mobile localized magnetic field generator to generate a motion box that includes the heart 18 and/or area of interest 38. The magnetic field generator 76 can have a thickness of 5 to 20 centimeter and contain magnetic transmitting elements $96^1$, $96^2$, $96^3$ strong enough to generate magnetic field at typical distance of 30 to 70cm. The magnetic field generator 76 can also have a magnetic field shield 82 that significantly reduces the magnetic field at the area of the x-ray transmitter 86 which can typically be located 5 cm to 50 cm from the magnetic field generator 76.

Embodiments are described herein of various apparatuses, systems, and/or methods. Numerous specific details are set forth to provide a thorough understanding of the overall structure, function, manufacture, and use of the embodiments as described in the specification and depicted in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment of a localized magnetic field generator has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An apparatus for generating a magnetic field for tracking of an object, comprising the following:
   a hand-held localized magnetic field generator, wherein the hand-held localized magnetic field generator includes:
      a magnetic field shield having a first side and a second side; and
      a plurality of magnetic transmitting elements located proximate to the magnetic field shield and on the first side of the magnetic field shield, wherein the hand-held localized magnetic field generator is configured to generate a magnetic field and to control the magnetic field in an area of interest and configured to control the magnetic field in a separate area, wherein:
         the separate area is displaced from the area of interest and includes a magnetic field-disrupting component,
         the object is located in the area of interest, and
         the magnetic field is capable of being directed toward the area of interest by hand.

2. The apparatus of claim 1, wherein the hand-held localized magnetic field generator is movable with respect to a patient examination table and wherein:
   the magnetic field shield forms a planar surface; and
   the plurality of magnetic transmitting elements are located proximate to the planar surface and on a first side of the planar surface.

3. The apparatus of claim 2, wherein the magnetic field shield is located between the plurality of magnetic transmitting elements and the magnetic field-disrupting component.

4. The apparatus of claim 1, wherein the magnetic field shield comprises a planar layer of material formed from a material selected from the group consisting of a magnetically permeable material and a conductive material.

5. The apparatus of claim 1, wherein the magnetic field shield comprises at least two planar layers of material, wherein one layer of material is a magnetically permeable material and the other layer of material is a conductive material.

6. The apparatus of claim 1, wherein the hand-held localized magnetic field generator further includes a front plate and a back plate, wherein:
   the front plate is located on the first side of the magnetic field shield;
   the back plate is connected to or integral with the magnetic field shield, wherein the magnetic field shield and the plurality of magnetic transmitting elements are enclosed by the front plate and the back plate;
   the magnetic field shield includes a lip formed around a perimeter of the magnetic field shield; and the lip is formed on a same side of the magnetic field shield as the plurality of magnetic transmitting elements are located.

7. The apparatus of claim 6, wherein the lip generally extends perpendicularly from the planar surface of the magnetic field shield.

8. The apparatus of claim 6, wherein a length between the planar surface of the magnetic field shield and a top of the lip is in a range of 0.1 to 2.0 times a distance between the planar surface and a top of the plurality of magnetic transmitting elements.

9. The apparatus of claim 1, wherein the plurality of magnetic transmitting elements are configured as synchronized magnetic transmitting elements which are grouped together and are configured to act as a single transmitting element and to produce a magnetic field at a same frequency, or which are grouped together and are configured to act as different magnetic transmitting elements and to produce a different magnetic field at different frequencies with respect to the single transmitting element and with respect to one another.

10. An apparatus for generating a magnetic field for tracking of an object, comprising the following:
 a hand-held localized magnetic field generator, wherein the hand-held localized magnetic field generator includes:
  a magnetic field shield that defines a planar surface and a lip formed around a perimeter of a first side of the planar surface; and
  a plurality of magnetic transmitting elements that are located proximate to the planar surface and on the first side of the planar surface, wherein the mobile localized magnetic field generator is configured to generate a magnetic field directed perpendicular to and away from the first side of the planar surface on which the magnetic transmitting elements are located,
 wherein the hand-held localized magnetic field generator is configured to control the magnetic field in an area of interest and configured to control the magnetic field in a separate area, and the magnetic field is capable of being directed toward the area of interest by hand.

11. The apparatus of claim 10, wherein:
 the separate area is displaced from the area of interest and includes a magnetic-field disrupting component; and
 the area of interest includes the object.

12. The apparatus of claim 10, wherein the hand-held localized magnetic field generator generates an asymmetric magnetic field directed perpendicular to and away from the first side of the planar surface on which the magnetic transmitting elements are located.

13. The apparatus of claim 12, wherein the magnetic transmitting elements include at least three magnetic transmitting elements.

* * * * *